United States Patent [19]

Fort et al.

[11] 3,972,225
[45] Aug. 3, 1976

[54] SAMPLING SYSTEM FOR POWER GENERATORS

[75] Inventors: Emil M. Fort, Murrysville; Thomas D. Kaczmsrek; David C. Phillips, both of Pittsburgh, all of Pa.

[73] Assignee: Westinghouse Electric Corporation, Pittsburgh, Pa.

[22] Filed: Dec. 19, 1973

[21] Appl. No.: 426,391

[52] U.S. Cl. ................................. 73/28; 73/150 R; 73/343 R; 73/421.5 R; 340/237 R; 340/411
[51] Int. Cl.² ..................... G01N 1/22; G01N 33/32
[58] Field of Search ......... 73/28, 421.5, 1 F, 432 R; 340/237 R, 214, 409, 410, 411; 310/68 B, 68 C

[56] References Cited
UNITED STATES PATENTS

| | | | |
|---|---|---|---|
| 2,727,203 | 12/1955 | Zeitlin et al. | 340/237 S |
| 3,304,783 | 2/1967 | Quigley | 73/28 |
| 3,521,276 | 7/1970 | Raber | 340/409 |
| 3,702,561 | 11/1972 | Carson et al. | 73/1 F |
| 3,807,218 | 4/1974 | Carson et al. | 73/432 R |
| 3,845,480 | 10/1974 | Steinberg et al. | 340/237 S |

Primary Examiner—S. Clement Swisher
Attorney, Agent, or Firm—R. D. Fuerle

[57] ABSTRACT

A sampling system monitors a gas stream of a power generator and automatically samples the gas stream if its characteristics indicate that a material in the power generator is being thermally degraded. A gas stream monitoring device generates a first signal if it detects degradation occurring. A time-delay relay determines whether the first signal is continuous, and if it is the relay acts to prevent the monitor from monitoring the gas stream. If the first signal then terminates, a second signal is generated which activates an alarm and permits gas to flow into a sampling device. The sampling device has three sections which collect large particles, small particulates, and vapors and gases. The products collected can be analyzed to determine which material in the power generator was thermally degraded.

13 Claims, 2 Drawing Figures

SAMPLING SYSTEM FOR POWER GENERATORS

BACKGROUND OF THE INVENTION

Large power generators occasionally fail due to thermal degradation of various materials, particularly organic insulation. Since an early detection of the insulation failure is essential to the prevention of a large-scale burn-out of the generator, monitoring devices are used which monitor the gas stream that flows through the generator. Presently, most monitors work by detecting particulates in the gas stream, which are formed when insulation is being thermally degraded. When the monitor detects degradation products and generates a signal, the flow of detectable particulates to the monitor is manually terminated to determine whether the signal is genuine or is due to a malfunction in the monitor. If the signal then terminates it is assumed to be genuine and the generator is shut down and the repair is made.

Since down time on a large generator can cost over $100,000 a day it is important to locate the insulation failure and repair it quickly. Over 50 different meterials are used in generators including regular and modified epoxies, polyesters, silicones, phenolics, etc. and unless the failure is easily visible, it may be very difficult to locate.

SUMMARY OF THE INVENTION

We have found that if the gas stream is sampled when the monitor indicates that a failure is occurring, the products collected can be analyzed to determine which material in the generator was failing. Since the location of the various materials is known, the search for the failure is considerably shortened.

We have also found that the sampling can be done automatically, so that when the monitor produces a signal it can be checked for authenticity and the sample taken without human interference.

Finally, we have found that a particular sampling device, which separates the products of the gas stream into particles 10 microns or greater, particulates less than 10 microns, and gases, is particularly useful in facilitating the analysis.

DESCRIPTION OF THE INVENTION

Figure 1:
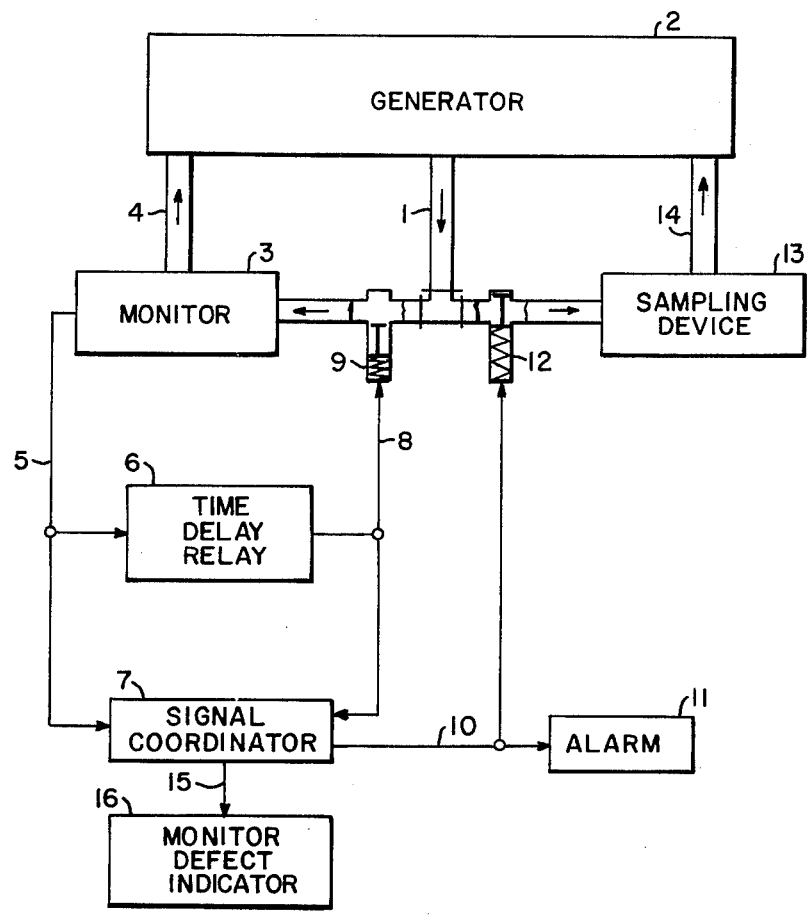
FIG. 1 is a diagram showing a presently preferred sampling system according to this invention.

In FIG. 1 conduit 1 carries gas from a gas stream of generator 2 to monitor 3 where it is monitored then returned to the generator through conduit 4.

Monitor 3 checks the gas stream for any characteristic which indicates that thermal degradation of a material in the generator is occurring. (The thermal degradation may be due to primary failure of the material, or may be a secondary failure which indicates that arcing or some other problem is occurring in the generator.) Typically, the monitor checks the level of particulates in the gas stream. Particulates, which are small particles or condensed gases (i.e., liquids, aerosols) less than about 10 microns in size, are formed when organic materials thermally degrade. In fact, some of the materials in the generator may be coated with substances which produce large quantities of particulates at low temperatures to aid in the early detection of insulation failure. The monitor may also detect the failure of materials by checking the vapors in the gas stream, its pH, its optical density or optical absorbence, or other characteristics or combination of characteristics.

Referring to FIG. 1 again, when the monitor detects failure of a material it generates a first signal, typically an electrical signal, which passes through line 5 to time-delay relay 6 and signal coordinator 7.

Insulation occasionally falls off or is abraded off by friction and some of this dust can be vaporized by the moving parts of the generator. If these dust particles are present in sufficient quantities they can cause monitor 3 to produce spurious signals for brief periods. These signals do not indicate a genuine material failure and must be ignored. Time-delay relay 6 therefore is not activated unless it receives a continuous signal for a predetermined length of time, typically at least about 15 seconds. It then produces a signal in line 8 which passes to signal coordinator 7 and to signal blocker 9.

Since stopping a generator and searching for insulation failure is a very expensive undertaking, monitor 3 must first be checked to determine that it is operating correctly. Depending on the type of monitor used, signal blocker 9 therefore terminates the flow of gas to the monitor or more preferably filters out of the gas stream the particulates or gases that activate the monitor.

If the first signal from the monitor then terminates, signal coordinator 7 generates a second signal which passes through line 10 to alarm 11 and solenoid valve 12 which controls the flow of the gas stream to sampling device 13 then back to the generator through conduit 14. Note that signal coordinator is first "armed" by a signal from time-delay relay and then is "fired" by the termination of the signal from the monitor. Should the signal from the monitor not terminate shortly after signal blocker 9 is activated, then signal coordinator 7 sends a signal through line 15 to monitor defect indicator 16 which indicates by light, alarm, etc. that the monitor is defective.

The signal coordinator preferably ceases to produce a signal after a sufficient period of time has passed to permit sampling device 13 to collect the material needed for analysis. Solenoid valve 12 then shuts off the supply of gas to sampling device 13. For the device of FIG. 2 a gas flow of about 5 to about 15 minutes at a rate of about 130 cubic feet per hour is usually adequate to collect a sufficient sample for analysis. Alarm 11, however, can remain active until someone turns it off and stops the generator. Alternatively, the signal in line 10 can be used to shut down the generator automatically.

In actual practice monitor 3, signal blocker 9, time-delay relay 6, signal coordinator 7, monitor defect indicator 16, and even alarm 11, solenoid valve 12, and sampling device 13 can be combined into a single piece of apparatus which is attached to the generator. Also, as an additional check, it may be desirable to have the signal coordinator produce a second signal only when signal-blocker 9 is deactivated and monitor 3 again generates a continuous signal in line 5. The entire system, of course, may be provided with a reset switch to return all parts to their original condition after activation. It should also be noted that the "signals" may be the absence or decrease of an electric current or other signal as well as its presence.

Sampling device 13 may be a balloon-like device which is filled by the gas stream, or another type of collector. Particularly advantageous in the sampling device shown in FIG. 2 because that device separates the particulates from the larger particles and the gases, and it is the particulates which are most useful in analyzing which material was degraded.

Figure 2:
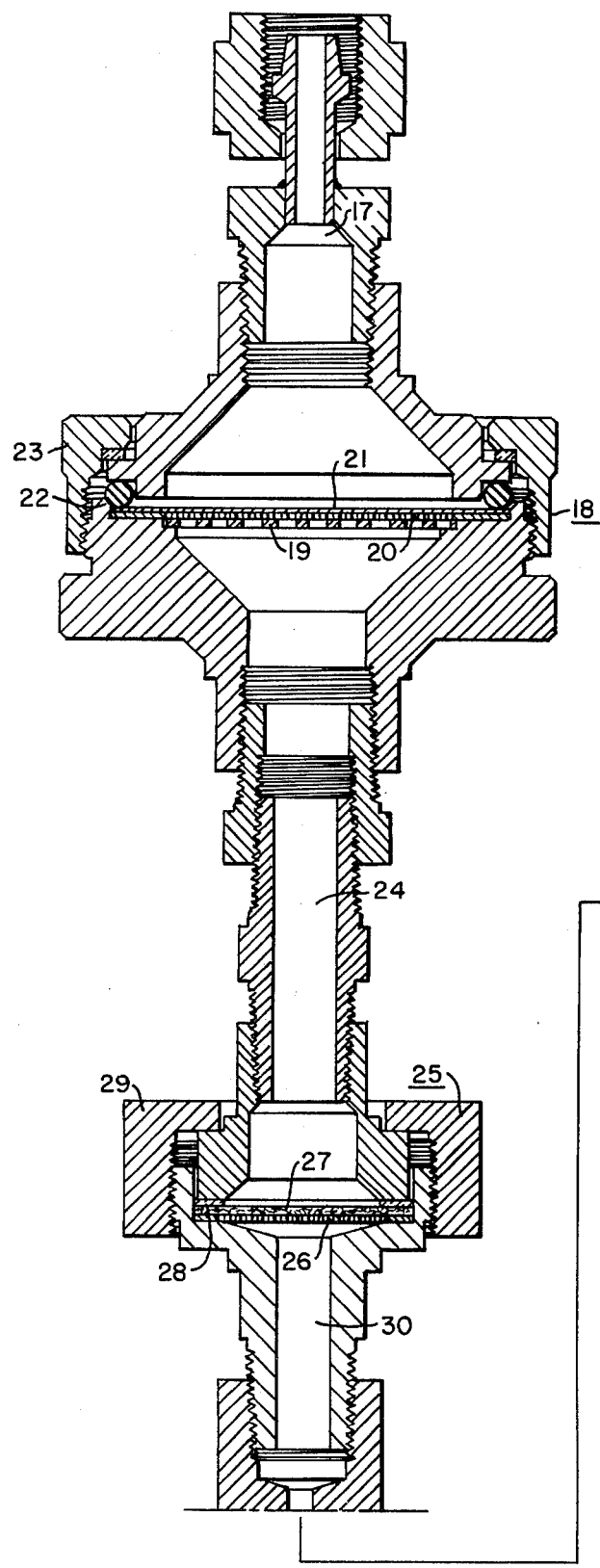
FIG. 2 is a side view in section of a certain sampling device according to this invention.
Figure 2:
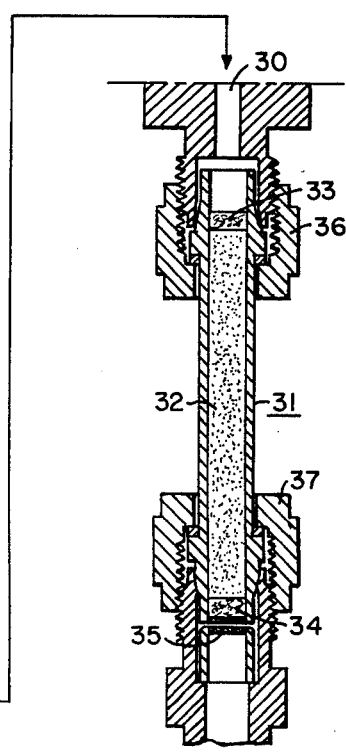

In FIG. 2 gas enters line 17 to particle filter chamber 18 where particles (i.e., greater than about 10 microns) are filtered out of the stream. The filter shown consists of grid 19 which supports screen 20 which supports particle collector 21. The filter is held in place by gaskets 22 and 21 and can be removed for analysis by unscrewing ring 23.

The gas stream then passes through line 24 to particulate filter chamber 25 where particulates (i.e., less than about 10 microns) are filtered out of the stream. The filter consists of screen 26 which supports particulate collector 27 of glass fiber, polypropylene, or other suitable material. Collector 27 is held in place by gasket 28 and can be removed for analysis by unscrewing ring 29.

The gas stream then passes through line 30 to vapor trap 31. The vapor trap contains absorbing material 32 held in place by glass wool plugs 33 and 34 and wire screen 35 which prevents the material from being blown out by gas pressure. The absorbing material 32 can be removed for analysis by unscrewing nuts 36 and 37. The absorbing material 32 may be any material which absorbs gas, such as activated carbon, silica gel, alumina, etc. but a modified ethylvinylbenzene-divinylbenzene copolymer sold by Waters Co. under the trademark "Porapak R" is preferred primarily because it is relatively insensitive to the water vapor normally present in a generator atmosphere, which tends to mask the analysis of other trapped gases.

While the particles should be filtered before the particulates, and the particulates filtered before the gases, other arrangements than that of FIG. 2 are also possible. For example, a sieve system of filters could be used to look at particular-sized particles which may be useful in analysis. Different absorbent filters can be used, each absorbing a particular gas, and the arrangement for gas absorbers can be in parallel instead of in series.

Although the sampling device of FIG. 2 is the presently-existing embodiment, it is contemplated that that embodiment will be improved upon. For example, an improved sampling device would be completely sealed and could only be opened easily by the person who is to perform the analysis. Also, an improved device would be made of less expensive materials, such as plastics, and would be disposable after use.

The analysis is made using a mass spectrometer and/or other standard techniques, by comparing the results of the analysis to the results of analyzing the decomposition products of known generator material. For example, each material used in the generator is slowly heated. When the monitor detects decomposition products a sample is collected and analyzed, for example, by a mass spectrometer. The mass spectrometer produces a chart of the molecular weight versus quantity for each decomposition product produced by a particular material. The charts for the materials used in the generator are then compared to the chart of the unknown samples and the unknown resin is thereby identified. A "map" of the generator shows the location of each material used.

It is also contemplated that the insulation and other materials of the generator be divided into a predetermined number of sectors, and that each sector be painted with a substance which thermally decomposes to produce decomposition products distinct from those of any other sector. The exact location of the failure can therefore then be determined.

We claim:

1. A sampling system comprising:
  A. gas stream-monitoring means for detecting the thermal degradation of materials by monitoring a gas stream exposed to the products of said thermal degradation, and for generating a first signal when said thermal degradation is detected;
  B. analysis means for automatically determining whether said gas stream monitoring means is functioning properly when said first signal is generated and if so, for automatically generating a second signal; and
  C. sampling means for automatically sampling said gas stream when said second signal is generated.

2. A sampling system according to claim 1 wherein said second signal also activates an alarm.

3. A sampling system according to claim 1 wherein said sampling means includes a filter system which comprises, in series,
  A. a particle filter for filtering particles greater than about 10 microns;
  B. a particulate filter for filtering particulates less than about 10 microns; and
  C. a vapor trap for absorbing gases.

4. A sampling system according to claim 3 wherein said sampling means includes a solenoid valve which controls the flow of said gas stream to said filter system.

5. A sampling system according to claim 1 wherein said analysis means comprises
  A. a time-delay relay which generates a third signal when said first signal has been generated continuously for a predetermined length of time;
  B. means for preventing said gas stream monitoring means from monitoring said gas stream when said second signal is generated; and
  C. coordinating means for generating said second signal when said third signal is generated and said first signal is not generated.

6. A sampling system according to claim 5 wherein said coordinating means ceases to generate said second signal after a predetermined period of time of sufficient length to permit said sampling means to collect a sample adequate for analysis.

7. A sampling system according to claim 5 wherein said coordinating means generates a fourth signal when said third signal is generated and said first signal does not terminate shortly after said third signal is generated, said fourth signal indicating that said monitor is defective.

8. In combination, a power generator having a gas stream and a sampling system for sampling said gas stream which comprises, series,
  A. a large particle filter for filtering particles greater than about 10 microns;
  B. a small particulate filter for filtering particulates less than 10 microns; and
  C. a vapor trap for absorbing gases.

9. A sampling system according to claim 1 wherein said gas stream is a cooling gas stream in an electrical generator.

10. A sampling system according to claim 9 wherein said second signal also shuts down said power generator.

11. A sampling system according to claim 1 wherein said analysis means does not begin determining whether said gas stream monitoring means is functioning properly until said first signal has been generated continuously for a predetermined length of time.

12. A sampling system according to claim 1 wherein said analysis means comprises means for preventing said gas stream monitoring means from monitoring said gas stream and for generating said second signal if said first signal ceases.

13. A sampling system according to claim 1 wherein said analysis means comprises means for preventing said gas stream monitoring means from monitoring said gas stream and for generating said second signal if said first signal ceases and then returns when said gas stream monitoring means is no longer prevented from monitoring said gas stream.

\* \* \* \* \*

UNITED STATES PATENT AND TRADEMARK OFFICE
CERTIFICATE OF CORRECTION

PATENT NO. : 3,972,225
DATED : August 3, 1976
INVENTOR(S) : Emil M. Fort, et al

It is certified that error appears in the above-identified patent and that said Letters Patent are hereby corrected as shown below:

Column 1, line 22, delete "meterials" and substitute -- materials --.

Column 2, line 7, delete "abraided" and substitute -- abraded --.

Column 3, line 9, delete "kets" and substitute -- ket --.

Column 3, line 9, after "and" insert -- particle collector --.

Column 3, line 61, delete "ples" and substitute -- ple --.

Claim 8, line 3, after "comprises," insert -- in --.

Signed and Sealed this

Tenth Day of January 1978

[SEAL]

Attest:

RUTH C. MASON
Attesting Officer

LUTRELLE F. PARKER
Acting Commissioner of Patents and Trademark